United States Patent [19]

Toda et al.

[11] Patent Number: 4,818,771

[45] Date of Patent: Apr. 4, 1989

[54] DIPHENIC ACID BIS(DICYCLOHEXYLAMIDE) FOR CLOTHRATE COMPOUND, PROCESS FOR PRODUCING THE SAME

[75] Inventors: Fumio Toda, Onsen; Ayako Sekikawa, Hatano; Hideo Sugi, Yokohama; Kenji Tahara, Atsugi, all of Japan

[73] Assignee: Kurita Water Industries, Ltd., Tokyo, Japan

[21] Appl. No.: 941,004

[22] Filed: Dec. 12, 1986

[30] Foreign Application Priority Data

Dec. 17, 1985 [JP] Japan ................................. 60-283860

[51] Int. Cl.$^4$ ......................... A61L 3/00; C02B 1/18; C07C 103/24
[52] U.S. Cl. ................................. 514/616; 534/558; 562/488; 564/142; 260/544 P
[58] Field of Search ......................... 564/156; 514/616

[56] References Cited

PUBLICATIONS

Gilman et al., "Organic Syntheses", Collective vol I, pp. 222 to 224, (1932), 2nd Ed.
Kissling, Chemical Abstracts, vol. 36, 992,3, (1942).
Vorshau et al., Chemical Abstracts, vol. 80, #59912d, (1974).

*Primary Examiner*—Floyd D. Higel
*Attorney, Agent, or Firm*—Frank J. Jordan; C. Bruce Hamburg; Manabu Kanesaka

[57] ABSTRACT

Diphenic acid bis(dicyclohexylamide) represented by the following formula:

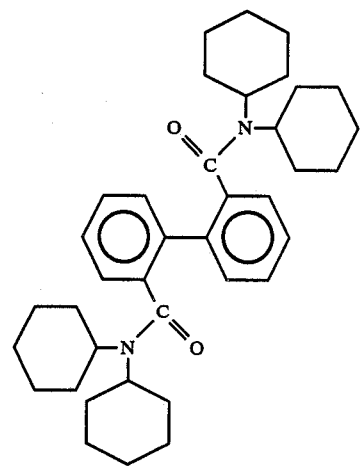

A process for producing diphenic acid bis(dicyclohexylamide) represented by the above formula, which comprises dimerizing a diazonium salt of o-aminobenzoic acid in the presence of a reducing agent, followed by acidification to give 2,6'-dicarboxylbiphenyl; converting this dicarboxylic acid to 2,6'-dichloroformylbiphenyl by chlorination; and reacting this acid chloride with dicyclohexylamine.

Sustained release antimicrobial compositions comprising a clathrate compound consisting of a microbial agent and diphenic acid bis(dicyclohexylamide) represented by the above formula.

7 Claims, 2 Drawing Sheets

DIPHENIC ACID BIS(DICYCLOHEXYLAMIDE) FOR CLOTHRATE COMPOUND, PROCESS FOR PRODUCING THE SAME

FIELD OF THE INVENTION AND RELATED ART STATEMENT

This invention relates to diphenic acid bis(dicyclohexylamide), to a process for producing the same, and to sustained release antimicrobial compositions using the same.

Slime of animal and plant or germ as mentioned below tends to deposit in cooling-water systems of general industrial facilities and water systems of the paper and pulp industry, often causing various hazards.

In general cooling-water systems, deposition of slime of zoogloea, alga and filamentous fungi reduces thermal efficiency, adversely affects circulation of water, and induces corrosion of metal parts.

In the paper and pulp industry, slime of bacteria, filamentous fungi and yeast occurs mainly in the paper mill process. This enters into pulp slurry as impurities, thus degrading the quality of final products, leading to paper breakage to greatly reduce production efficiency, and causing many other troubles. Usage of recirculated water has increased in recent years, and this makes slime control an issue of greater importance in this field.

In thermoelectric power plants, ironworks and other facilities using seawater, marine algae and bacteria, mytilus, protochordata and other living matters tend to deposit at seawater intakes and on the internal surfaces of cooling pipes, thus lowering water-intake and cooling efficiency. These deposits are also detached and carried by flowing water and often clog other parts of facility, such as tubes of heat exchangers and strainers, retarding flow of water and degrading the performances of the entire system.

To prevent such troubles caused by slime deposition, it is customary to use antimicrobial agents (slime control agents) because of low cost and easy treatment. The most popularly used materials are water-soluble slime control agents, such as isothiazoline compounds. Of these, 5-chloro-2-methyl-4-isothiazolin-3-one (hereinafter abbreviated as "CMI") represented by formula (I) shown below has exceptionally high antimicrobial activity and is extensively used as slime controller, bactericide, algicide and fungicide in coolingwater systems, paper and pulp industry, swimming pools and other water systems.

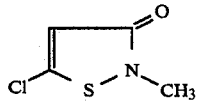

CMI is generally produced (1) by halogenation of β-thioketamide in an inert organic ester, such as ethyl acetate, or (2) by treatment of a β-substituted thiocyanoacrylamide or thiosulfatoacrylamide with an acid, followed by halogenation.

Either one of the two processes mentioned above, (1) and (2), fails to selectively give CMI, but affords mixtures containing, as impurity, 2-methyl-4-isothiazolin-3-one (hereinafter abbreviated as "MI") represented by formula (II) shown below—a substance having lower antimicrobial activity ten times less than CMI.

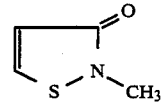

It is also impossible for the prior art to selectively isolate CMI from the reaction mixtures.

In addition, CMI, although it has excellent antimicrobial activity, is highly irritant to the skin, requiring extra care in handling. When used in water, it tends to react with some organic substances contained (e.g., amines and reducing substances) to lose its activity, and hence it is difficult to maintain the antimicrobial activity over long periods. Like CMI as described above, the water-soluble antimicrobial agents conventionally used are very unsatisfactory in terms of handling and antimicrobial effect because of their toxicity, tendency of rapidly loosing activity and high solubility in water. We formerly found that the problems associated with conventional slime controllers are mentioned above can be solved by new sustained release antimicrobial compositions comprising a clathrate compound consisting of a water-soluble antimicrobial agent and 1,1,6,6-tertaphenyl-2,4-hexadiyne-1,6-diol, and applied such compositions for a patent (Japanese Patent Application No. 173771/1984; hereinafter referred to as "prior application"). Outstanding antimicrobial effects could be achieved by the antimicrobial compositions of the prior application.

OBJECTS AND SUMMARY OF THE INVENTION

A primary object of this invention is to provide a new compound which is very useful as a host molecule that forms clathrate compounds with antimicrobial agents, and a process for producing the same.

A further object of this invention is to provide sustained release antimicrobial compositions capable of maintaining exceptionally high microbial activity over very long periods.

Another object of this invention is to provide sustained release antimicrobial compositions which are low in toxicity and easy to handle.

These objects can be achieved by (1) diphenic acid bis(dicyclohexylamide) represented by the following formula,

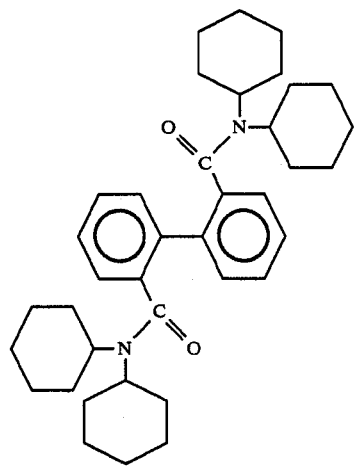

(2) by a process for producing the same which comprises the following steps: (a) dimerizing a diazonium salt of o-aminobenzoic acid in the presence of a reducing agent, followed by acidification to give 2,6'-dicarboxylbiphenyl, (b) chlorinating 2,6-dicarboxylbiphenyl thus obtained to form 2,6'-dichloroformylbiphenyl, and (c) reacting 2,6'-dichloroformylbiphenyl thus obtained with dicyclohexylamine; and (3) by a sustained release antimicrobial composition comprising a clathrate compound consisting of diphenic acid bis(dicyclohexylamide) and an antimicrobial agent.

Studies in search of new clathrate compounds not disclosed in the prior application have led us to succeed in synthesizing the above-mentioned novel compound, diphenic acid bis(dicyclohexylamide), and to find that this compound is effective as a host molecule capable of forming clathrate compounds, together with microbial agents, that can exhibit outstanding effects as sustained release compositions. This invention was accomplished based on these findings.

DETAILED DESCRIPTION OF THE PREFERRED EMBODIMENTS

Figure 1:
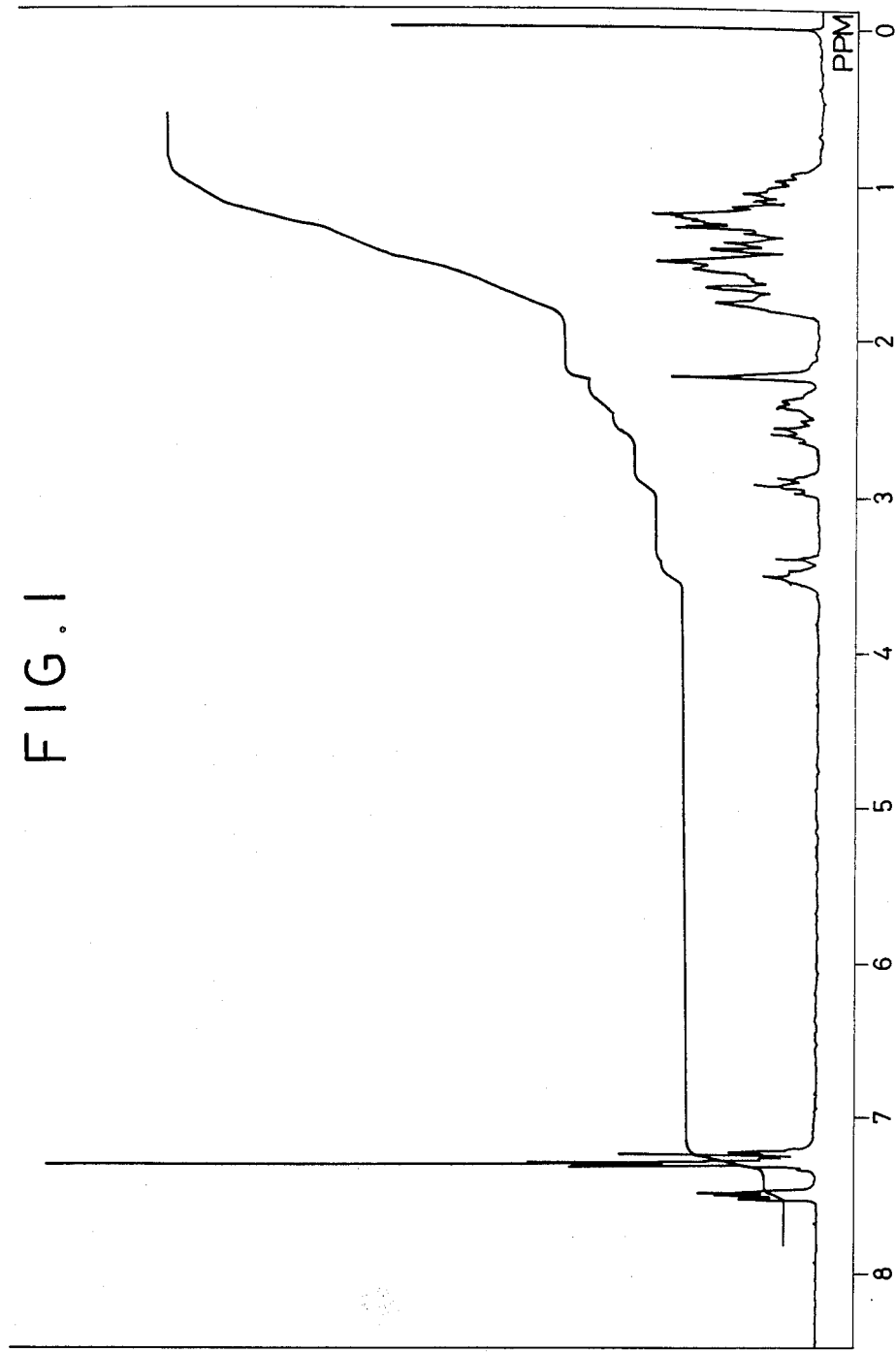
FIG. 1 is an NMR spectrum of diphenic acid bis(dicyclohexylamide) of this invention.
Figure 2:
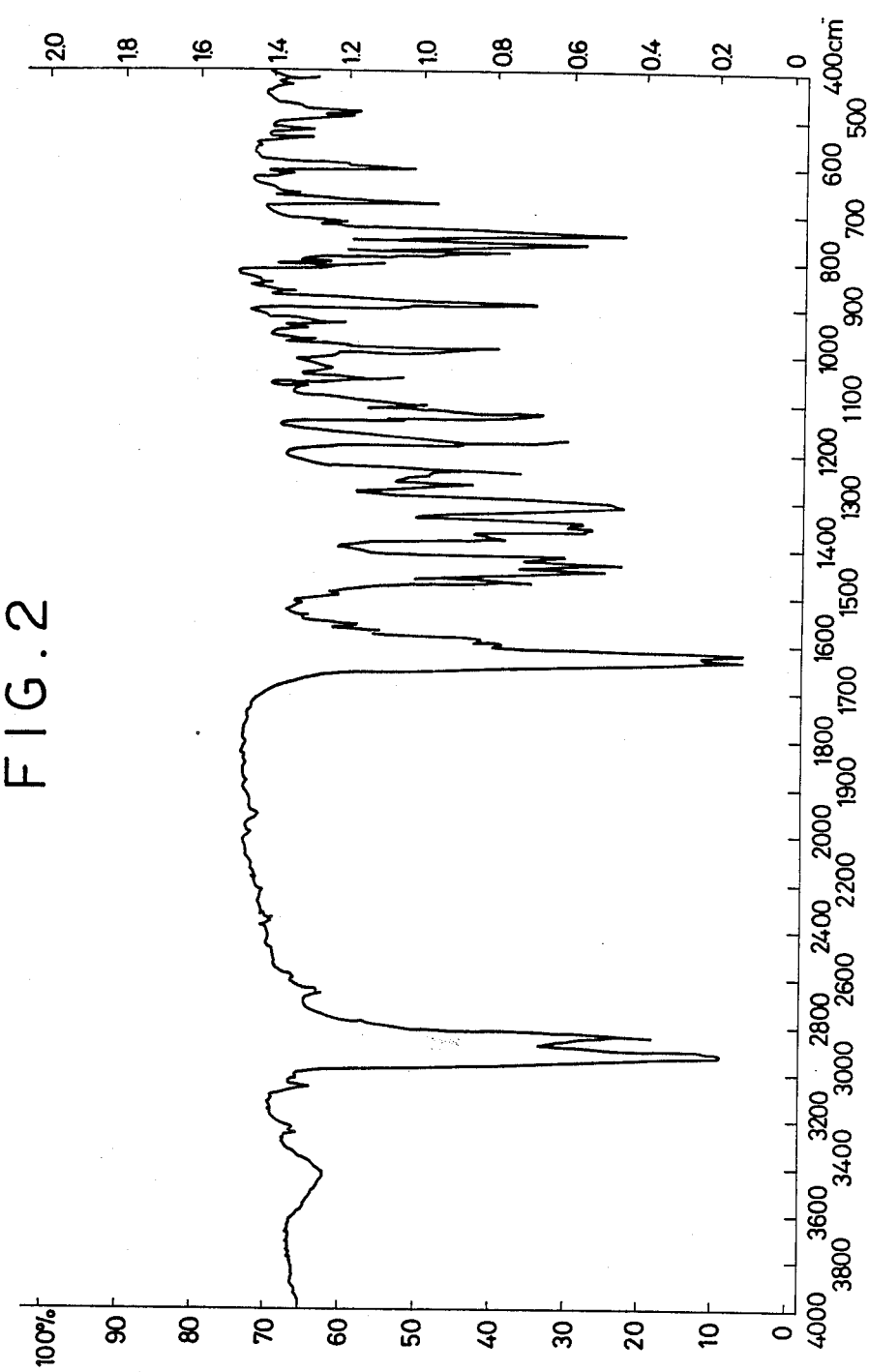
FIG. 2 shows its IR spectrum.

Diphenic acid bis(dicyclohexylamide) of this invention is a novel compound represented by the following structural formula and having NMR and IR spectra as shown in FIGS. 1 and 2, respectively.

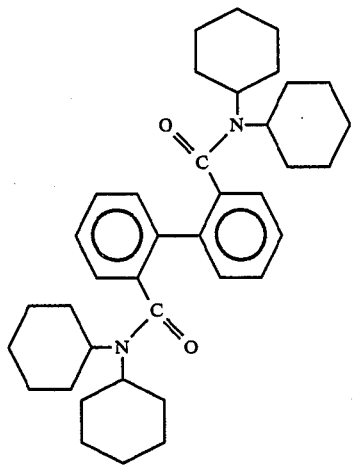

The process for producing this new compound is outlined below. Sodium nitrite is added in small portions to a solution of o-aminobenzoic acid (anthranilic acid) in hydrochloric acid to convert the amine to diazonium chloride (diazotization). Since the diazonium salt is ready to decompose and this decomposition reaction is accelerated with rising temperature, the diazotization should preferably be carried out at a low temperature in the range from 0° to 5° C. The amounts of hydrochloric acid and sodium nitrite to be used should preferably be in slight excess of their stoichiometric amounts.

The solution of diazonium salt thus formed is submitted to the next step without further treatment. It is slowly added to a reducing agent comprising a cuprous complex salt to give the corresponding dimer, followed by acidification by addition of hydrochloric acid to afford 2,6'-dicarboxylbiphenyl. This product can be obtained as white to creamcolored needles melting at 225°–228° C. by treatment with activated carbon.

2,6'-Dicarboxylbiphenyl thus prepared is then converted to the corresponding acid dichloride by heating, together with a large excess of thionyl chloride, under reflux for several hours. 2,6'-Dichloroformylbiphenyl thus formed is separated out upon distillation of excess thionyl chloride under reduced pressure.

A solution of this compound in a suitable solvent (for example, benzene) is added dropwise to a solution of dicyclohexylamine under ice cooling, the mixture is allowed to stand for several hours, and the crystals of diphenic acid bis(dicyclohexylamide) which separate out are collected and recrystallized from benzene-acetone.

The reaction steps involved in the process of this invention outlined above are shown below.

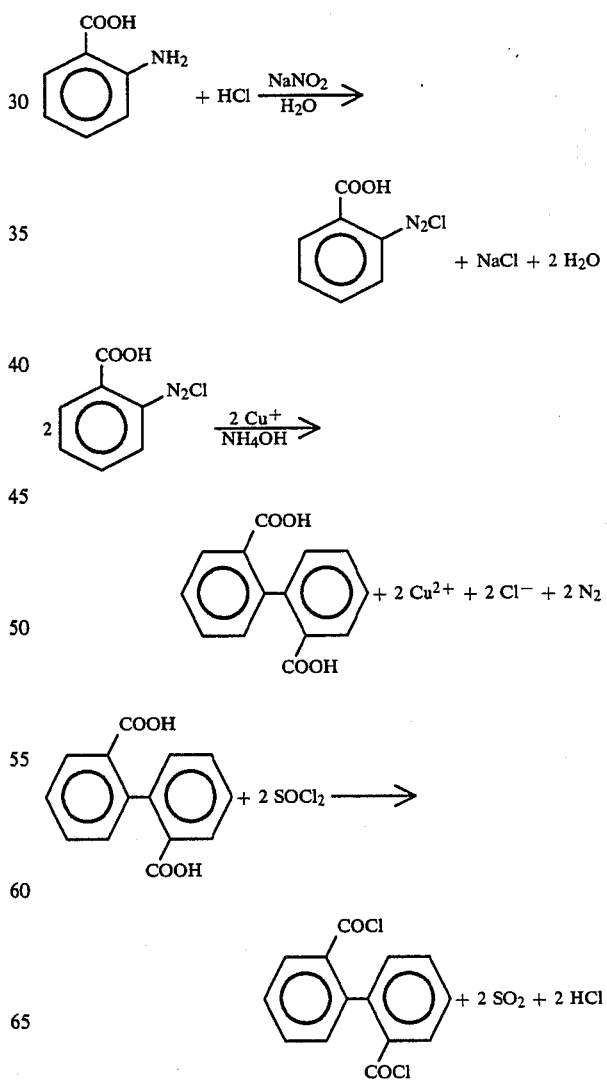

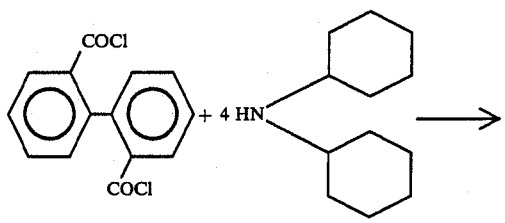

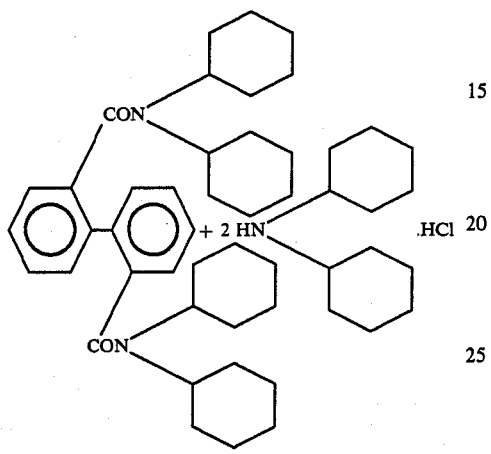

An illustrative procedure for preparing diphenic acid bis(dicyclohexylamide) is detailed in Preparative Example 1 shown later.

This compound is useful as a host molecule capable of forming clathrate compounds with various antimicrobial agents.

Described below are sustained release antimicrobial compositions obtained by the use of diphenic acid bis(-dicyclohexylamide).

The sustained release antimicrobial compositions of this invention are compositions comprising a clathrate compound consisting of an antimicrobial agent and diphenic acid bis(dicyclohexylamide).

The antimicrobial agent used in this invention may be any antimicrobial agent that can form a clathrate compound together with diphenic acid bis(dicyclohexylamide). Typical examples include, among others, CMI, methylene bis (thiocyanate) (hereinafter abbreviated as "MBTC"), methyl thiocyanate (hereinafter abbreviated as "MTC"), benzoisothiazolone (hereinafter abbreviated as "BiT") and hydrazine.

The clathrate compounds of this invention can be prepared by using the following materials, (a), (b) and (c):

(a) A solution of diphenic acid bis(dicyclohexylamide) in an ether or ester solvent
(b) An antimicrobial agent, such as CMI, MBTC, MTC and BiT
(c) A mixture of antimicrobial agent and other impurities Slow mixing of (a) with (b) or with (c) gives a colorless or tan suspension, from which the objective clathrate compound can be isolated by filtration or other usual method.

This preparative method is very advantageous in that, even when an antimicrobial agent containing much impurities is used as starting material, only the effective compound is selectively included in the final clathrate compound.

The antimicrobial agent, such as CMI, is selectively included as guest molecule in diphenic acid bis(dicyclohexylamide) [hereinafter abbreviated as DPA(DCHA)$_2$] as host molecule, and separates out in the form of a clathrate compound. The reactions normally proceed according to the schemes shown below to give clathrate compounds with the compositions as shown, although there may be slight variations depending on reaction conditions.

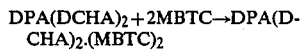

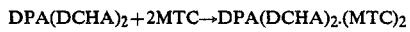

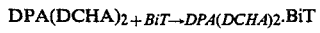

The clathrate compounds of this invention thus prepared are normally powdery solid and can be easily shaped into any desired form (e.g., tablets). Since the antimicrobial agent is included in the host molecule, toxicity is low and handling is also very easy.

The sustained release antimicrobial compositions of this invention may contain, other than a clathrate compound as defined above, a binder, solvent, carrier, humectant, filler and other additives, as required. The content of clathrate compound should preferably be 1 weight % or larger, more preferably in the range from 1 to 100 weight %, and most preferably in the range from 5 to 50 weight %.

The sustained release antimicrobial compositions of this invention may be used in various ways as listed below.

(1) Water being treated is allowed to pass through a column packed with a sustained release antimicrobial composition of this invention.

(2) The composition of this invention is charged in bags or cartridges that are insoluble in water but are permeable to water, and the bags and cartridges are set submerged or afloat in the water system being treated.

(3) The composition of this invention, either powdery or suitably shaped, is allowed to flow in the water system being treated in the form of dispersion.

(4) The composition of this invention is admixed to a resin coating or the like and coated on the surfaces of equipment placed in service in the water system.

(5) The composition of this invention is fixed to the surfaces of objects being protected by a suitable means.

Diphenic acid bis(dicyclohexylamide) disclosed in this invention is a novel compound which serves as a host molecule for CMI and other antimicrobial agents.

The sustained release antimicrobial compositions of this invention comprise a clathrate compound composed of an antimicrobial agent included in diphenic acid bis(dicyclohexylamide), and therefore have the following advantages:

(1) Since the effective component gradually comes into solution, its antimicrobial activity lasts over very long periods.

(2) It can be shaped into any desired form (e.g., tablets) for ease of handling.

(3) It can provide safe and better working environment because of the lowered toxicity and reduced irritative action.

(4) There is no tendency of losing antimicrobial activity due to reaction of the effective component with other substances.

The industrial usefulness of the sustained release antimicrobial composition of this invention is extremely high.

The following Examples further illustrate this invention but are not intended to limit its scope; any changes or modifications may be made within the spirit of this invention.

PREPARATIVE EXAMPLE 1

Preparation of Diphenic Acid Bis(dicyclohexylamide):

[Reaction No. 1]

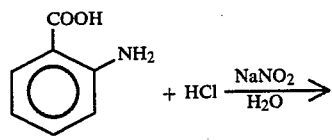

o-Aminobenzoic acid (50 g), concentrated hydrochloric acid (72 ml) and water (150 ml) were placed in a 1-liter, three-necked flask, and the mixture was agitated to give a suspension. Diazotization was conducted by adding dropwise a solution of $NaNO_2$ (26.3 g) in 350 ml water to this suspension over a period of 30 minutes while maintaining the temperature at 0° to 520 C. by external cooling with water.

[Reaction No. 2]

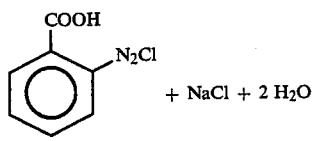

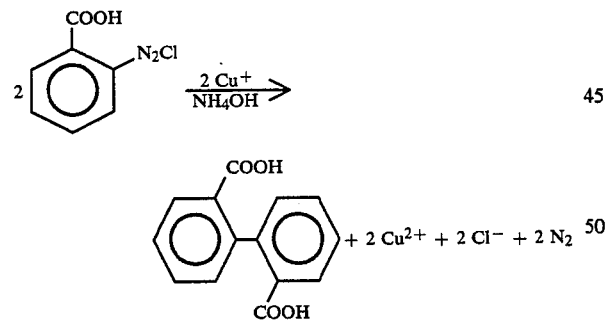

A solution of $CuSO_4$ (126 g) in 500 ml water was cooled to 10° C., and saturated ammonia water (210 ml) was added to this cooled solution (solution A). Separately, a solution of $(NH_2OH)_2.H_2SO_4$ (42 g) in 120 ml water was cooled to 10° C., and 6N-NaOH (85 ml) was added to this cooled solution (solution B). Solutions A and B were mixed together by stirring to give a reducing agent. The color turned pale blue after mixing of the two solutions.

The reducing agent prepared above was placed in a flask, the solution of diazonium salt obtained in Reaction No.1 was added dropwise at a rate of 10 ml per minute to effect reduction, and then the reaction mixture was heated under reflux and acidified by addition of concentrated hydrochloric acid (250 ml). The resulting mixture was allowed to stand overnight, and the crystals which separated out were collected by filtration, affording 38 grams of crude product.

The crude product was suspended in 200 ml water, $NAHCO_3$ (40 g) was added to the suspension to dissolve the dicarboxylic acid, and the insoluble matters are filtered off by suction. Activated charcoal (0.5 g) was added to the filtrate, the mixture was boiled and then filtered by gravity, and the filtrate was acidified by addition of 6N-HCl, giving 2,6'-dicarboxylbiphenyl as cream-colored needles (yeild: 34.8 g, 78.6%).

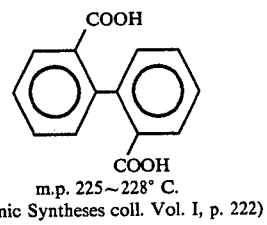

m.p. 225~228° C.
(Organic Syntheses coll. Vol. I, p. 222)

[Reaction No. 3]

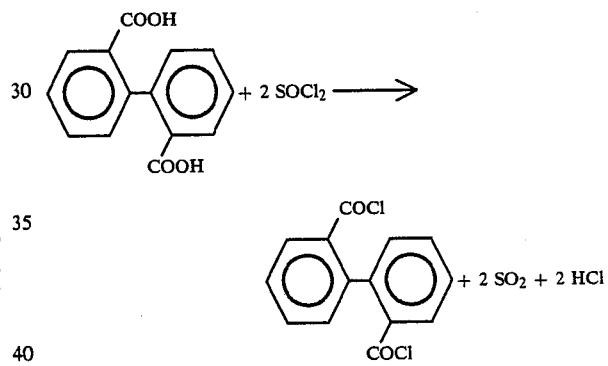

The needles obtained in Reaction No. 2 (34.8 g) and $SOCl_2$ (100 ml) were placed in a 200 ml, round-bottomed flask, the mixture was heated under reflux for four to six hours, and excess $SOCl_2$ was distilled off under reduced pressure, giving crystals of 2,6'-dichloroformylbiphenyl (yield: 39.4 g, 99%).

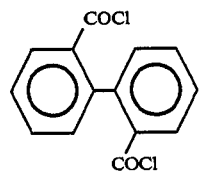

[Reaction No. 4]

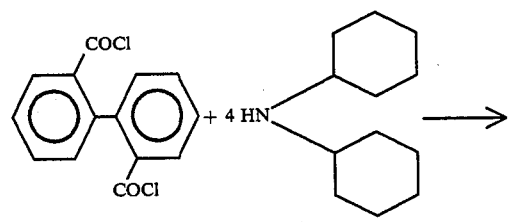

-continued

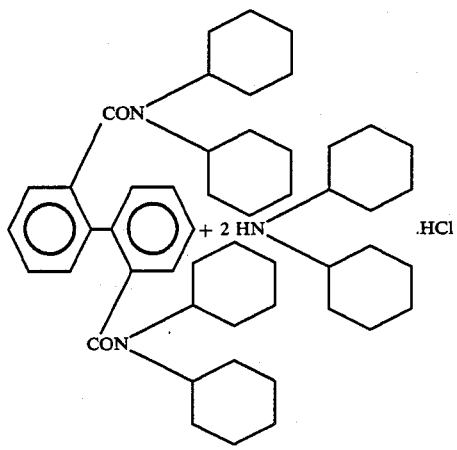

A solution of the crystals obtained in Reaction No.3 (39.4 g) in 200 ml benzene was slowly added dropwsie to a solution of dicyclohexylamine (102.1 g) in 100 ml benzene under ice cooling with occasional stirring. The reaction mixture was thoroughly agitated and then allowed to stand for six hours, followed by extraction with hot benzene. Crystals of diphenic acid bis(dicyclohexylamide) were separated out by adding acetone to the benzene extract.

The crystals obtained above (yield: 63.8 g, 80%) had a melting point of 204°–208° C., gave an NMR spectrum (CDCl$_3$–CD$_3$OD) and IR spectrum (KBr tablet) as shown in FIG. 1 and FIG. 2, respectively, and were identified as

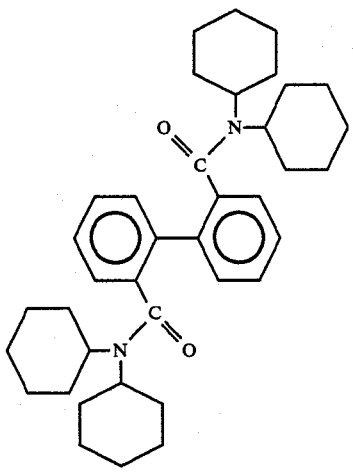

EXAMPLE 1

Preparation of [DPA(DCHA)$_2$]$_3$.CMI

To a solution of DPA(DCHA)$_2$ (2.19 g, 0.385×10$^{-2}$ mol) in 20 ml of ethyl acetate, were added CMI (0.9 approximately 0.6×10$^{-2}$ mol) and MI (0.26 g) with stirring, the turbid reaction mixture thus obtained was allowed to stand at room temperature for 16 hours, and the precipitate which separated out was collected on filter paper by filtration.

NMR analysis revealed that this product consists of DPA(DCHA)$_2$ and CMI at a molar ratio of 3:1 and at a weight ratio of 92.0:8.0. It was also demonstrated by elemental analysis that no MI is contained in this product. CMI Dissolution Test:

Samples of [DPA(DCHA)$_2$]$_3$.CMI (1) and CMI (2) were each placed in a 0.8μ membrane filter bag (0.1 g as CMI for each), each bag was immersed in 1 liter of pure water under stirring, and the CMI concentration in water was measured at definite time intervals. The result is summarized in Table 1.

TABLE 1

| | Changes in CMI Concentration with Time (Unit: ppm) | | | | |
|---|---|---|---|---|---|
| Time Elapsed | 10 min | 1 hr | 2 hr | 4 hr | 24 hr |
| (1) | 7 | 45 | 70 | 86 | 100 |
| (2) | 100 | 100 | 100 | 100 | 100 |

EXAMPLE 2

Preparation of DPA(DCHA)$_2$.(MBTC)$_2$

A solution of DPA(DCHA)$_2$ (2.02 g, 0.352×10$^{-2}$ mol) in 30 ml of n-butyl ether was mixed with a solution of MBTC (0.904 g, 0.697×10$^{-2}$ mol) in 10 ml of n-butyl ether with stirring, the turbid reaction mixture thus obtained was allowed to stand at room temperature for 16 hours, and the precipitate which separated out was collected on filter paper by filtration.

NMR analysis revealed that this product consists of DPA(DCHA)$_2$ and MBTC at a molar ratio of 1:2 and at a weight ratio of 68.9:31.1.

MBTC Dissolution Test

Samples of DPA(DCHA)$_2$.(MBTC)$_2$ (1) and MBTC (2) were each placed in a 0.8μ membrane filter bag (0.1 g as MBTC for each), each bag was immersed in 1 liter of pure water under stirring, and the MBTC concentration in water was measured at definite time intervals. The result is summarized in Table 2.

TABLE 2

| | Changes in MBTC Concentration with Time (Unit: ppm) | | | | | |
|---|---|---|---|---|---|---|
| Time Elapsed | 10 min | 1 hr | 2 hr | 4 hr | 8 hr | 24 hr |
| (1) | 0 | 18 | 32 | 54 | 90 | 100 |
| (2) | 100 | 100 | 100 | 100 | 100 | 100 |

EXAMPLE 3

Preparation of DPA(DCHA)$_2$.(MTC)$_2$

To a solution of DPA(DCHA)$_2$ (2.03 g, 0.352×10$^{-2}$ mol) in 20 ml of n-butyl ether, was added MTC (1 ml, 1.37×10$^{31}$ $^2$ mol) with stirring, the mixture thus obtained was allowed to stand at room temperature for three days, and the resulting turbid mixture was filtered through filter paper.

NMR analysis of the solid collected above revealed that it consists of DPA(DCHA)$_2$ and MTC at a molar ratio of 1:2 and at a weight ratio of 94.0:6.0.

MTC Dissolution Test

Samples of DPA(DCHA)$_2$.(MTC)$_2$ (1) and MTC (2) were each placed in a 0.8μ membrane filter bag (0.1 g as MTC for each), each bag was immersed in 1 liter of pure water under stirring, and the MTC concentration in water was measured at definite time intervals. The result is summarized in Table 3.

TABLE 3

Changes in MTC Concentration with Time
(Unit: ppm)

| Time Elapsed | 10 min | 1 hr | 2 hr | 4 hr | 8 hr | 24 hr |
|---|---|---|---|---|---|---|
| (1) | 0 | 16 | 26 | 46 | 76 | 100 |
| (2) | 100 | 100 | 100 | 100 | 100 | 100 |

EXAMPLE 4

Preparation of DPA(DCHA)$_2$.BiT

A solution of DPA(DCHA)$_2$ (1.9 g, 0.334×10hu −2 mol) in 30 ml of n-butyl ether was mixed with a solution of BiT (0.8 g, 0.533×10$^{-2}$ mol) in 10 ml of n-butyl ether with stirring, the brown, turbid reaction mixture thus obtained was allowed to stand at room temperature for 16 hours, and the precipitate which separated out was collected on filter paper by filtration.

NMR analysis revealed that the precipitate obtained above consists of DPA(DCHA)$_2$ and BiT at a molar ratio of 1:1 and at a weight ratio of 79.1:20.9.

BiT Dissolution Test

Samples of DPA(DCHA)$_2$.BiT (1) and BiT (2) were each placed in a 0.8μ membrane filter bag (0.1 g as BiT for each), each bag was immersed in 1 liter of pure water under stirring, and the BiT concentration in water was measured at definite time intervals. The result is summarized in Table 4.

TABLE 4

Changes in BiT Concentration with Time
(Unit: ppm)

| Time Elapsed | 10 min | 1 hr | 2 hr | 4 hr | 8 hr | 24 hr |
|---|---|---|---|---|---|---|
| (1) | 0 | 13 | 24 | 40 | 66 | 100 |
| (2) | 100 | 100 | 100 | 100 | 100 | 100 |

As can be seen from the data shown in Tables 1 through 4, each of the antimicrobial agents began to be dissolved out upon immersion of filter bag in water with samples (2) (antimicrobial agent alone), while the antimicrobial agents were dissolved out but very slowly with samples (1) (clathrate compounds). This clearly indicates the outstanding characteristics of the sustained release antimicrobial compositions of this invention to exhibit their effect over prolonged periods.

What is claimed is:

1. Diphenic acid bis(dicyclohexylamide) represented by the following formula:

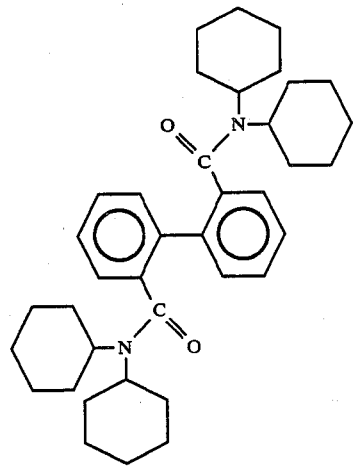

2. A sustained release antimicrobial composition comprising a clathrate compound consisting of an antimicrobially effective amount of an antimicrobial agent with diphenic acid bis(dicyclohexylamide) represented by the following formula:

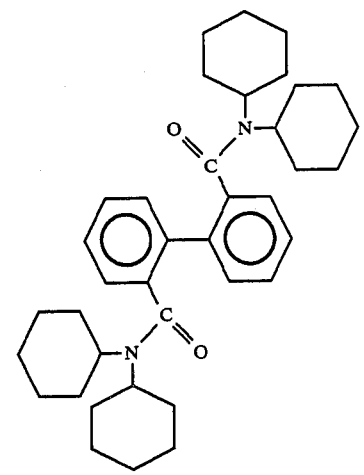

3. The sustained release antimicrobial composition as defined in claim 2, wherein said antimicrobial agent is at least one member selected from the group consisting of 5-chloro-2-methyl-4-isothiazolin-3-one, methylene bis(-thiocyanate), methyl thiocyanate, benzoisothiazolone and hydrazine.

4. The sustained release antimicrobial composition as defined in claim 3, wherein said antimicrobial agent is 5-chloro-2-methyl-4-isothiazolin-3-one.

5. The sustained release antimicrobial composition as defined in claim 2, wherein the content of said clathrate compound is in the range from 1 to 100 weight %.

6. The sustained release antimicrobial composition as defined in claim 2, wherein the content of said clathrate compounds is in the range from 5 to 50 weight %.

7. The sustained release antimicrobial composition as defined in claim 2, wherein said composition is provided in the form of tablets.

* * * * *